United States Patent [19]

Eicher et al.

[11] Patent Number: 5,336,817

[45] Date of Patent: * Aug. 9, 1994

[54] METHOD OF PREPARING 1,1,1,2-TETRAFLUOROETHANE

[75] Inventors: Johannes Eicher, Garbsen; Karl-Heinz Fazniewscy, Lehrte; Matthias Rieland; Werner Rudolph, both of Hanover all of Fed. Rep. of Germany

[73] Assignee: Solvay Fluor und Derivate GmbH, Hanover, Fed. Rep. of Germany

[*] Notice: The portion of the term of this patent subsequent to Dec. 15, 2009 has been disclaimed.

[21] Appl. No.: 950,497

[22] Filed: Sep. 25, 1992

[30] Foreign Application Priority Data

Oct. 8, 1991 [DE] Fed. Rep. of Germany ..... 04133247

[51] Int. Cl.⁵ .................. C07C 17/08; C07C 19/08
[52] U.S. Cl. .................... 570/168; 570/165; 570/167
[58] Field of Search .................. 570/168, 165, 167

[56] References Cited

U.S. PATENT DOCUMENTS

| | | | |
|---|---|---|---|
| 2,462,359 | 2/1949 | Calfee et al. | 260/653 |
| 3,413,362 | 11/1968 | Otaku | 260/653.6 |
| 3,810,948 | 5/1974 | Meussdoerffer et al. | 260/653.6 |
| 4,258,225 | 3/1981 | Feiring | 570/168 |
| 4,374,289 | 2/1983 | Van Der Puy et al. | 570/168 |
| 4,383,128 | 5/1983 | Van Der Puy et al. | 570/165 |
| 4,967,024 | 10/1990 | Gumprecht et al. | 570/188 |
| 5,015,791 | 5/1991 | Rao | 560/168 |

FOREIGN PATENT DOCUMENTS

| | | |
|---|---|---|
| 48544 | 3/1982 | European Pat. Off. . |
| 297947 | 1/1989 | European Pat. Off. . |
| 300724 | 1/1989 | European Pat. Off. . |
| 348190 | 12/1989 | European Pat. Off. . |
| 349190 | 1/1990 | European Pat. Off. . |
| 0451746 | 10/1991 | European Pat. Off. ......... 570/188 |
| 1245348 | 7/1967 | Fed. Rep. of Germany . |
| 1945655 | 3/1971 | Fed. Rep. of Germany . |
| 2139993 | 2/1973 | Fed. Rep. of Germany . |
| 2234305 | 1/1974 | Fed. Rep. of Germany . |
| WO 89/12616 | 12/1989 | PCT Int'l Appl. . |
| WO 89/12617 | 12/1989 | PCT Int'l Appl. . |
| 8912614 | 12/1989 | PCT Int'l Appl. ......... 570/188 |
| 8912615 | 12/1989 | PCT Int'l Appl. ......... 570/188 |

OTHER PUBLICATIONS

Feiring, "Chemistry in Hydrogen Fluoride v. Catalysts for Reaction of HF with Halogenated Olefins", *J. Fluorine Chem.*, 19:7–18 (1979).

Andrews et al., "A Simple Synthesis for Carbon–13 Enriched Fluorochloromethanes and Fluoromethanes", *J. Fluorine Chem.*, 13:273–78 (1979).

Yarwood et al., *J. Chem. Soc.*, 1965 pp. 7481–7499.

*Chemical Abstracts*, vol. 63, No. 11349f-g (1965).

Martynov et al., Translation from Zhurnal Obshchei Khimii, vol. 35, No. 6, pp. 967–969, Jun. 1965.

*Primary Examiner*—Alan Siegel
*Attorney, Agent, or Firm*—Evenson, McKeown, Edwards & Lenahan

[57] ABSTRACT

A method of preparing $CH_2FCF_3$ from fluorodichloroethylene using a catalytically active niobium, tantalum or molybdenum fluorosulfonate compound or a catalyst mixture which comprises a niobium, tantalum or molybdenum halide and a sulfonic acid derivative.

11 Claims, No Drawings

METHOD OF PREPARING 1,1,1,2-TETRAFLUOROETHANE

BACKGROUND OF THE INVENTION

The invention relates to a method for preparing 1,1,1,2-tetrafluoroethane (R134a), $CH_2FCF_3$.

There is an increasing need for environmentally compatible halogenated hydrocarbons. $CH_2FCF_3$ has proved to be one of these. This compound may be used, for instance, as a refrigerant or propellant. There remains a need, however, for simple methods of producing this compound on an industrial scale at high conversion rates.

SUMMARY OF THE INVENTION

It is an object of the present invention to provide a new method for preparing $CH_2FCF_3$ which is simple to perform.

Another object of the invention is to provide a new method of preparing $CH_2FCF_3$ which is well suited for industrial scale production.

A further object of the invention is to provide a new method of producing $CH_2FCF_3$ at high conversion rates.

These and other objects of the invention are achieved by providing a method of preparing $CH_2FCF_3$ comprising catalytically reacting $CHF=CCl_2$ with hydrofluoric acid (HF) in liquid phase in the presence of a catalytically active preparation comprising a niobium fluorosulfonate compound, a tantalum fluorosulfonate compound, a molybdenum fluorosulfonate compound, or a mixture of a niobium, tantalum or molybdenum pentahalide and a sulfonic acid derivative selected from the group consisting of fluorosulfonic acid and perfluoro(C1–C12)alkanesulfonic acid, the hydrofluoric acid being used in at least the quantity stoichiometrically required to react the $CHF=CCl_2$ to $CH_2FCF_3$, and the molar ratio of $CHF=CCl_2$ to catalytically active compound being from about 10:1 to 1:100.

DETAILED DESCRIPTION OF PREFERRED EMBODIMENTS

The method according to the present invention for preparing $CH_2FCF_3$ uses a catalytically active preparation containing niobium, tantalum or molybdenum. The method of the invention is characterized in that $CHFCl=CCl_2$ is reacted with hydrofluoric acid in the liquid phase, the reaction being catalyzed by a catalytically active preparation which contains a niobium fluorosulfonate compound, a tantalum fluorosulfonate compound, a molybdenum fluorosulfonate compound and/or a mixture of a niobium, tantalum or molybdenum pentahalide and a sulfonic acid derivative, selected from fluorosulfonic acid and perfluoro (C1–C12)-alkanesulfonic acid, the hydrofluoric acid being used at least in the quantity which is stoichiometrically necessary and the molar ratio of starting compound to catalytically active compound being between about 10:1 and 1:100.

According to one variant of the method according to the invention, therefore, a niobium, tantalum or molybdenum fluorosulfonate compound is used. Preferably in this variant a niobium fluorosulfonate compound or a tantalum fluorosulfonate compound is used. Very particularly preferably, a compound corresponding to the formula (I)

$$MX_n(FSO_3)_{5-n} \quad (I)$$

wherein M represents niobium or tantalum, X represents halogen, and n is a number from 0 to 4, preferably from 1 to 4, is used as the catalyst. X is preferably chlorine or fluorine, and n is very particularly preferably a number from 2 to 4.

The preparation of such compounds is known. For example, E. Hayek, J. Puschmann and A. Czaloun describe the preparation of $TaCl_3(FSO_3)_2$ from tantalum pentachloride and fluorosulfonic acid and evaporation of excess fluorosulfonic acid in *Monatshefte Chemie* 85:359–63 (1954). The compound can also be prepared from tantalum pentachloride and fluorosulfonic acid derivatives, for instance fluorosulfonic ethyl ester. Reaction products of niobium pentachloride and fluorosulfonic acid are viscous or gelatinous. H. C. Clark and H. J. Emeleus in *J. Chem. Soc.* 1958, pages 190 to 195, in particular page 193, suggest this is $NbCl_3(FSO_3)_2$.

Clark et al. [op. cit.] also describe the preparation of $TaF_3(FSO_3)_2$ and $NbF_3(FSO_3)_2$ from tantalum pentafluoride or niobium pentafluoride and sulfur trioxide at room temperature.

W. V. Cicha and F. Aubke describe the preparation of further tantalum and niobium fluoride fluorosulfonate compounds in *J. Fluorine Chem.* 47:317–32 (1990)

$Ta(FSO_3)_5$ and $Nb(FSO_3)_5$ may be prepared by oxidation of the respective metal powder with bis-(fluorosulfuryl)-peroxide in fluorosulfonic acid. When reacting niobium metal powder, $NbF_2(FSO_3)_3$ is also produced as a byproduct.

$TaF_4(FSO_3)$ can be prepared, for example, by a ligand exchange reaction between $Ta(FSO_3)_5$ and four mole equivalents of tantalum pentafluoride.

According to a particularly preferred embodiment of this variant, the catalytically active compound is a tantalum-chloride-fluorosulfonate compound or a niobium-chloride-fluorosulfonate compound which has been obtained by the reaction of tantalum pentachloride or niobium pentachloride with fluorosulfonic acid in a molar ratio of 1:1 to 1:4. Instead of fluorosulfonic acid, fluorosulfonic acid derivatives which react with tantalum pentachloride or niobium pentachloride with the substitution of chloride by fluorosulfonate, for instance fluorosulfonic esters, may also be used.

According to another particularly preferred embodiment of this variant, a tantalum-fluoride-fluorosulfonate compound or a niobium-fluoride-fluorosulfonate compound which has been obtained by reacting tantalum pentafluoride or niobium pentafluoride with sulfur trioxide is used as the catalytically active compound. Alternatively, corresponding compounds are used which have been obtained by reacting tantalum pentachloride or niobium pentachloride with fluorosulfonic acid or a fluorosulfonic acid derivative which reacts with tantalum pentachloride or niobium pentachloride with substitution of chloride by fluorosulfonate, for instance a fluorosulfonic ester, in a molar ratio of 1:1 to 1:4 and subsequent chlorine-fluorine exchange.

In the variant described above, at most small undesirable quantities of pentahalides are still present in the preparation. If desired, the fluorosulfonate compound may be produced in the presence of $CHF=CCl_2$, which then acts as a diluent.

According to another variant of the method according to the invention, the reaction is catalyzed by a catalytically active preparation which contains a mixture of niobium pentahalide, tantalum pentahalide or molybdenum pentahalide and a sulfonic acid derivative. Preferred pentahalides are niobium pentahalide and tantalum pentahalide, in particular niobium pentachloride, niobium pentafluoride, tantalum pentachloride or tantalum pentafluoride. Preferred sulfonic acid derivatives are fluorosulfonic acid and perfluorinated (C1–C3) sulfonic acids such as trifluoromethanesulfonic acid, in particular fluorosulfonic acid. Preferably in this variant the pentahalide and sulfonic acid derivative are present in a molar ratio of 5:1 to 1:5, in particular 1:1 to 1:5. The sequence of mixing of $CHF=CCl_2$, HF pentahalide and sulfonic acid derivative is not critical.

According to another variant of the present invention, the reaction may be catalyzed by a compound which contains a niobium, tantalum or molybdenum fluorosulfonate compound, a niobium, tantalum or molybdenum pentahalide and a sulfonic acid derivative.

Of course, the catalytically active preparation may also contain a mixture of pentahalides of various of the aforementioned metals, a mixture of various sulfonic acid derivatives or a mixture of various fluorosulfonate compounds of the aforementioned metals. As used herein, the term "catalytically active compound" is intended to include such mixtures.

The molar ratio of starting compound to the fluorosulfonate compound or to the mixture of pentahalide and sulfonic acid derivative is between 10:1 and 1:100, as explained further above. If there is a catalyst mixture, the number of moles of the catalyst mixture is calculated by adding the numbers of moles of the metal halide and the sulfonic acid derivative If for instance 1 mole $CHF=CCl_2$ is reacted with hydrofluoric acid in the presence of a mixture of 0.5 mole niobium pentahalide and 0.5 mole fluorosulfonic acid, the molar ratio of the starting compound to the catalyst mixture in this case is 1:1.

Preferably the molar ratio of $CHF=CCl_2$ starting compound to catalyst or catalyst mixture is between 10:1 and 1:10, in particular between 2:1 and 1:5.

The molar ratio of $CHF=CCl_2$ and hydrofluoric acid is preferably between 1:10 and 1:100.

The quantity of hydrofluoric acid to be used may go beyond the quantity required for the addition of hydrofluoric acid and for the chlorine-fluorine exchange. If metal pentachlorides or metal pentabromides or metal halide fluorosulfonate compounds are used, it should be assumed that more or less an exchange of chlorine or bromine for fluorine takes place. If, therefore, for instance niobium pentachloride or tantalum pentachloride or $NbCl(FSO_3)_4$ or $TaCl(FSO_3)_4$ are contained in the preparation, they may possibly be present in the reaction mixture in the form of partially fluorinated or fluorinated metal compounds.

Particulars of the quantity of hydrofluoric acid to be used are to be understood in view of the above explanations in the sense that for each fluorine atom introduced into the substrate molecule, hydrofluoric acid advantageously is used in a quantity which corresponds at least to the stoichiometrically required amount, and additionally as much hydrofluoric acid as is required for any halogen-fluorine exchange of the metal halide. For simplicity, this definition is not referred to each time in the present invention.

In order to estimate what quantity of hydrofluoric acid is additionally necessary for this halogen-fluorine exchange which may occur, a person skilled in the art may first react the preparation containing metal halide or metal halide-fluorosulfonate compound with hydrofluoric acid. The quantity of hydrofluoric acid consumed and/or the quantity of hydrogen halide formed makes it possible to calculate what quantity of hydrofluoric acid is required over and above that required for the reaction of the hydrogen halide used.

The temperature during the reaction between $CHF=CCl_2$ and HF is preferably between 50° and 200° C. The pressure corresponds to or lies above the autogenous pressure, and is for instance up to 30 bar (absolute). The pressure and temperature are selected such that the reaction takes place in the liquid phase.

Moisture has a disrupting effect in the method according to the invention. The reaction is therefore desirably carried out under conditions which prevent a harmful quantity of water from being able to enter the reaction mixture. It is advantageous to use hydrofluoric acid which is substantially water-free. Depending on the quantity of hydrofluoric acid used, it may be recommended to dry the commercially available hydrofluoric acid before use. Furthermore, it is recommended to keep the apparatus used in as dry as possible a state. To this end, lines, reaction vessels, apparatus for processing and storing the product may be flushed with dry gases, for instance with dry air or dry nitrogen gas.

According to a preferred embodiment of the method according to the invention, the $CHF=CCl_2$ required for the reaction is prepared from $CHFClCHCl_2$ by cleaving off HCl. The HCl cleavage may be performed thermolytically with or without a catalyst or with bases, for instance alkali hydroxide, if desired in suitable solvents such as alcohols.

According to a very particularly preferred embodiment, first of all $CHFClCHCl_2$ is prepared by selective fluorination of $CHCl_2CHCl_2$ the resulting $CHFClCHCl_2$ is then converted into $CHF=CCl_2$ with cleavage of HCl, and the resulting $CHF=CCl_2$ is then reacted with hydrofluoric acid according to the method of the invention.

The selective fluorination of $CHCl_2CHCl_2$ is described, for instance, by I. V. Martynov and Yu. L. Kruglyak in *Zh. Obshch. Khim.* 35(6):967–69 (1965); *Chemical Abstracts* 63:11349 g (1965). The preferred selective fluorination agent is antimony trifluoride, the catalytic action of which may be additionally promoted by addition of antimony pentachloride. The reaction is advantageously performed at 130° to 220° C.

The method according to the invention may be performed in a batch process or continuously.

The reaction products may be worked up by passing them through a gas scrubber and subsequently subjecting them to fractional distillation.

The apparatus used for performing the method should be resistant to hydrofluoric acid, metal halides and fluorosulfonic acid derivatives. Components made of polytetrafluoroethylene (e.g. "Teflon TM") and special alloys such as "Hastelloy TM", a nickel alloy resistant to hydrofluoric acid, are used.

The method according to the invention is distinguished by a high conversion rate and high selectively, and may advantageously be performed in the liquid phase. Polymerization of the starting compound is not observed. If the process is carried out in accordance with the particularly preferred embodiments starting from $CHFClCHCl_2$, or even from $CHCl_2CHCl_2$, there is the additional advantage that the desired product can be produced from particularly inexpensive starting chemicals which are simple to prepare.

The following example is intended to illustrate the method of the invention in greater detail, without restricting its scope.

EXAMPLE

Preparation of 1 1 1 2-tetrafluoroethane from 1,1,2,2-tetrachloroethane with a tantalum-containing catalyst preparation.

1.1 Selective fluorination of 1,1,2,2,-tetrachloroethane.

The selective fluorination was performed in a 500 ml three-necked flask with a paddle mixer. The three-necked flask was connected via a 20 cm Vigreux column to a Liebig condenser. A receiving vessel connected to the condenser and to a cooling trap. The reaction vessel was heated by means of an oil bath.

168 g 1,1,2,2 -tetrachloroethane, 107 g SbF$_3$ and 7 g SbCl$_5$ were introduced into the three-necked flask with flushing with nitrogen. The contents of the flask were then heated with stirring. The oil bath was brought to a temperature of 205° C. over a period of 4.5 hours. Volatile constituents distilled from an oil bath temperature of 180° C. upwards. 108 g distillate were obtained. According to a gas chromatogram, the distillate consisted of 31.5% by weight CHFClCHCl$_2$. Furthermore, it contained 64.1% by weight of the starting material and 3.5% by weight C$_2$HFCl$_4$. The desired product was isolated by subsequent precision distillation.

1.2 HCl cleavage from CHFClCHCl$_2$

The reaction was carried out according to the method of J. Yarwood and W. J. Orville-Thomas, *J. Chem. Soc.* (1965), pages 7481 to 7499. Ethanolic potassium hydroxide solution was placed in a receptacle, and 28 g of the 1-fluoro-1,2,2-trichloroethane prepared in Example 1.1.1 were added thereto in drops. The resulting product was distilled off continuously. The product was subsequently purified by fractional distillation. 17 g of CHF=CCl$_2$ were obtained boiling at 37° C.

1.3 Reaction of CHF=CCl$_2$ and HF to form CH$_2$FCF$_3$.

Apparatus used

A laboratory autoclave of V4A steel (a steel alloyed with chromium, nickel and molybdenum) was used. The internal volume of this autoclave was 0.25 liters. The autoclave was equipped with a magnetic stirrer, an immersion tube through which the starting compounds could be metered in, and a thermometer pocket by means of which the internal temperature could be measured. Furthermore, the laboratory autoclave had a gas outlet, which was connected to a gas scrubber filled with water. The gas scrubber itself was connected to a low-temperature condensation apparatus.

Performance of the fluorination reaction 15 g TaCl$_5$ were introduced and 20 g hydrofluoric acid (HF) were condensed into the autoclave. The mixture was heated to 95° C., and the resulting HCl and the surplus hydrofluoric acid were discharged. Then 15 g FSO$_3$H and 15.5 g of the CHF=CCl$_2$ prepared in Example 1.2 and also 40 g HF were added. The reaction mixture was then heated to 110° C. for about 2 hours. A sample of the volatile organic compounds contained 65% 1,1,1,2-tetrafluoroethane and 1,1,2-trifluoro-1-chloroethane. The reaction mixture was then heated for another 3 hours to 150° C. Then volatile constituents were evaporated, passed through the gas scrubber, and the organic constituents leaving the gas scrubber were collected in the low-temperature condensation apparatus. Analysis of the condensed product indicated that it consisted of 92.1% by weight 1,1,1,2-tetrafluoroethane and 7.9% by weight trifluorochloroethane (approximately equimolar mixture of R133a and R133b). 1,1,1,2-tetrafluoroethane in pure form was isolated by further distillation.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A method of preparing CH$_2$FCF$_3$ comprising catalytically reacting CHF=CCl$_2$ with hydrofluoric acid in liquid phase in the presence of a catalytically active preparation comprising a niobium fluorosulfonate compound, a tantalum fluorosulfonate compound, a molybdenum fluorosulfonate compound, or a mixture of a niobium, tantalum or molybdenum pentahalide and a sulfonic acid derivative selected from the group consisting of fluorosulfonic acid and perfluoro (C1–C12) alkanesulfonic acid, the hydrofluoric acid being used in at least the quantity stoichiometrically required to react the CHF=CCl$_2$ to CH$_2$FCF$_3$, and the molar ratio of CHF=CCl$_2$ to catalytically active compound being from about 10:1 to 1:100.

2. A method according to claim 1, wherein said catalytically active preparation is a mixture of niobium pentahalide or tantalum pentahalide and fluorosulfonic acid.

3. A method according to claim 2, wherein the molar ratio of niobium pentahalide or tantalum pentahalide to fluorosulfonic acid is from 5:1 to 1:5.

4. A method according to claim 1, wherein said catalytically active preparation contains a tantalum or niobium fluorosulfonate compound corresponding to the formula (I)

$$MX_n(FSO_3)_{5-n} \qquad (I)$$

wherein X represents halogen, M represents niobium or tantalum, and n is a number from 0 to 4.

5. A method according to claim 1, wherein said reaction is carried out in the temperature range from about 50° to about 200° C.

6. A method according to claim 1, wherein the molar ratio of CHF=CCl$_2$ to hydrofluoric acid is from 1:10 to 1:100.

7. A method according to claim 1, wherein the molar ratio of CHF=CCl$_2$ to catalytically active compound is from about 10:1 to 1:10.

8. A method according to claim 1, further comprising prior to the step of reacting CHF=CCl$_2$ with hydrofluoric acid, a step of preparing CHF=CCl$_2$ by cleaving off HCl from CHFClCHCl$_2$.

9. A method according to Claim 8, further comprising prior to the step of cleaving off HCl from CHFClCCl$_2$H, a step of selectively fluorinating CHCl$_2$CHCl$_2$ to form CHFClCHCl$_2$.

10. A method according to Claim 9, wherein said selective fluorination step is effected using antimony trifluoride.

11. A method according to claim 10, wherein said selective fluorination step is carried out in the presence of a catalysis-promoting quantity of antimony pentachloride.

* * * * *